United States Patent [19]

Wyatt et al.

[11] Patent Number: 4,548,500
[45] Date of Patent: Oct. 22, 1985

[54] PROCESS AND APPARATUS FOR IDENTIFYING OR CHARACTERIZING SMALL PARTICLES

[76] Inventors: Philip J. Wyatt, 1939 Laguna St., Santa Barbara, Calif. 93101; Gregory M. Quist, 6750 El Colegio, Apt. #49, Goleta, Calif. 93117

[21] Appl. No.: 390,980

[22] Filed: Jun. 22, 1982

[51] Int. Cl.[4] ............................................. G01N 15/02
[52] U.S. Cl. ...................................... 356/336; 356/343; 364/525; 364/555
[58] Field of Search ............... 356/336, 338, 341, 343; 250/574; 364/525, 555

[56] References Cited

U.S. PATENT DOCUMENTS

| | | | |
|---|---|---|---|
| 3,770,351 | 11/1973 | Wyatt | 356/336 |
| 3,901,602 | 8/1975 | Gravatt, Jr. | 250/574 X |
| 4,070,113 | 1/1978 | Frazer et al. | 356/341 X |
| 4,173,415 | 11/1979 | Wyatt | 356/336 |

Primary Examiner—Davis L. Willis
Assistant Examiner—Matthew W. Koren

[57] ABSTRACT

An apparatus and process are described for the characterization and/or identification of individual microparticles based upon the measurement of certain optical observables produced as each particle passes through a beam of light, or other electromagnetic radiation. A fine beam of, preferably, monochromatic linearly polarized light passes through a spherical array of detectors, or fiber optics means to transmit incident light to a set of detector means, and a stream of particles intersects the beam at the center of the spherical array. Selected observables calculated from the detected scattered radiation are then used to recall specific maps, from a computer memory means, one for each observable. The common overlap region of said maps yields characterizing or identifying particle physical parameters such as size, mean refractive index, and shape. A method for rapidly discriminating non-spherically symmetric particles is also disclosed.

16 Claims, 6 Drawing Figures

PROCESS AND APPARATUS FOR IDENTIFYING OR CHARACTERIZING SMALL PARTICLES

The Government has rights in this invention pursuant to Contract No. DAAK11-81-C-0107 awarded by the U.S. Army Armament Research and Development Command. The invention described herein may be manufactured, used, and licensed by and for the Government for governmental purposes without payment to us of any royalty thereon.

DEFINITIONS

The term light, as used herein, refers in general to electromagnetic radiation of wavelengths varying from x-rays through the far infrared, i.e. a range from a few nanometers to about 50,000 nanometers.

The term microparticle, as used herein, includes but is not limited to a microparticle of organic or inorganic origin such as dust, smog particles, bacterial cells, viruses, antibodies, antigens, pollen, water droplets, liquid droplets, salt crystals, asbestos fibers, platelets, and mammalian cells such as blood.

The term aerosol particle, as used herein, shall mean a microparticle surrounded by a medium different in composition from itself. Usually, such a term will refer to a particle surrounded by a medium composed of a mixed gas such as air or a pure gas such as carbon dioxide or nitrogen. Most generally the surrounding medium could be a gas, or a liquid, or even a vacuum.

The term small particle shall mean microparticle.

BACKGROUND

Instrumentation capable of rapidly identifying individual aerosol particles at high sampling rates does not currently exist despite numerous practical applications and immediate need. The range of uses for such devices is enormous, spanning both civilian and military requirements. Historically, there are probably two major reasons for the absence of such units from the sophisticated electro-optical and electronic hardware available today.

First, of course, is the fact that particle identification per se is usually associated with concepts of chemical and spectroscopic analysis; viz. collecting the particles, reacting them with chemical and/or physical (electricity, heat, etc.) probes, and then analyzing the resultant spectra or reaction products. The very small size of each sample whose identification might be required (i.e., a single aerosol particle) makes such chemical approaches very difficult from an operational point of view. In the area of bacterial detection alone, for example, huge Federal resources were expended in the 1960's to build units that might collect and separate such particles from their ambient surroundings, maintain their viability, culture them or tag them with species specific fluorescent stains, and (eventually) yield the required detection alarms. Such systems were cumbersome, expensive, unable to operate under real time conditions, and generally ineffective. Another similar area of aerosol analysis that absorbed vast amounts of Federal funds in the 1970's related to the relatively simple detection of airborne asbestos fibers. The Environmental Protection Agency opted for "conventional" measurements of such particles such as X-ray spectroscopy and electron microprobe devices. When the impracticality of such approaches eventually became obvious, the EPA funded an optically oriented instrumentation technique developed by Leeds and Northrup. Large fibers were detected with the L&N Microtrac units, but unambiguous identification and application to smaller fibers were not obtainable.

The second historical reason for the lack of suitable aerosol identification instrumentation related to the huge amount of data handling that such units would have to perform. Until the advent of the microprocessor and, more importantly, the recently developed array processors, even the mere booking associated with the identification of thousands of particles was impossible from the practical point of view. These latter obstacles no longer exist, of course, and the availability of inexpensive, highly compact data handling hardware has resulted in considerably more attention being devoted to the real time aerosol identification problem.

Given the availability of suitable electronics, optical techniques are attractive as an instrumentation basis for an aerosol analyser, though not enough attention has been devoted to their practical implementation. Several particle counters and so-called "sizers" based on optical scattering techniques have been developed and marketed commercially during the past decade. But claims regarding the capability of these instruments to size particles accurately have been greatly exaggerated; probably because such measurements from the point of view of classical optical scattering have been considered simple and straightforward. For particles below a few thousand nanometers in diameter and/or exhibiting shape and structural irregularity and/or absorptive properties, Cooke and Kerker pointed out the shortcomings of these "conventional" optical analysers in 1975. Their analyses have been generally overlooked or ignored as both Federal Agencies (notably NASA and NOAA) and commercial instrument manufacturers continued to use their resources for the refinement of instrumentation in which they earlier had made large investments.

The desire to characterize aerosol particles by instrument means has invariably required some form of measurement that could at least yield a particle *size*. Optical methods have always seemed attractive in this regard and many instruments have been developed that incorporated an optical means of one sort or another to provide a size estimate. As alluded to by Cooke and Kerker, these optically-based particle counter/sizers do not generally yield correct answers, especially for submicron particle sizes. Particles in this latter size range, unfortunately, are among the most important types as they remain airborn for great periods of time, are responsible for major sources of visibility obscuration, and include important particles for the propagation of biological and chemical threats. More sophisticated optical approaches have also been developed which purport to be able to size particles well into the submicron region, but for the most part, they too have some serious shortcomings which preclude such measurement. Surprisingly, these flaws have very little to do with instrument design, but arise because of some simple oversight related to the underlying theory of the interaction of light with matter. An interesting example of this is the particle sizing interferometer (PSI) which yields extremely valuable information about large particles, and especially fibers. Unfortunately, for smaller particles, the fundamental assumption on which basis the system operates is invalid, viz. ". . . the light which is scattered by the particle is proportional to the observed flux illuminating it . . . ." Ever since Lorenz developed his theory to explain the scattering of light from spherical particles, it has been known that the amount of light scattered by such particles is not proportional to the particle's size. Indeed, for certain sizes and refractive index compositions, the amount of light intercepted and scattered by a particle can be many times the amount incident on its physical area, and this is especially true in the submicron (or resonance) region.

Now it has long been reasoned that if one could measure all of the light scattering properties of a single particle, one could in concept deduce its structure (shape, size, refractive index). Such measurements performed at a single wavelength are usually called the Stoke's parameters, or more generally, the Mueller matrices as discussed, for example by Thompson, et al in *Applied Optics*. However, it should be pointed out that these matrix elements (referred to as 4 states of incident polarization) are measured in *a plane*. Of the 16 assorted DLS patterns so recorded, only 7 are independent, corresponding to the 8 values of the two complex orthogonal amplitudes of the incident and scattered electric fields less a common phase of each. Insofar as single particles are concerned so elaborate a measurement does not seem necessary to deduce all of its optical parameters. Indeed, a single state of incident polarization may well yield equivalent data, when scattering measurements are recorded over the surface of a sphere rather than restricted to a plane. Be that as it may, after all the measurements have been made (if they can be made at all), the most difficult problem still remains: How can we deduce the particle's structure (shape, size, refractive index) from these measurements? In this disclosure we shall present a method and instrumentation design that will achieve this "inversion". But first we must explain what this means.

For the case of an inhomogeneous aerosol particle exhibiting spherical symmetry, there is a quantum mechanical analogue whose study has provided us useful guidance in the delineation of various systems parameters that are incorporated into our invention. R. Newton, for example, has shown that, within certain limits, the form of the scattering potential (analogous here to the dielectric composition of the scattering particle) may be deduced if a single phase shift be measured at all incident energies (all wavelengths), or if all the phase shifts be determined at a single energy (wavelength). The measurement of the phase shift $\delta_l$, would be achieved by measurement of the associated scattering amplitude $\exp(i\delta_l)$ for each value of $l$ yielding an effectively non-zero $\delta_l$. Experimentally, of course, one usually measures the scattered intensity which is proportional to the square of the magnitude of the total scattering amplitude. Thus the measurement of scattered intensity at a single wavelength does not provide for deduction of the total amplitude phase, nor does it permit the separation of the individual phase shift amplitude contributions, let alone their individual phases. Nevertheless, we generally assume that "embedded" in the measured scattered intensity, for a given state of incident polarization, is all the important phase shift information from which may be deduced the scattering particle's structure. Can indeed such measurements yield unique structural information?

It has generally been assumed for some time that the dielectric structure and composition of a spherically-symmetric particle can be deduced from a measurement (including various measurements at different incident polarizations) of the scattered light intensity over a reasonably broad range of scattering solid angles. Since the direct deduction of the phase shifts, and the reconstruction therefrom of the scattering particle's structure, is impossible, the usual method has consisted of parameterizing a spherically symmetric model and adjusting these parameters to obtain a least squares' fit to the data. This method has been applied successfully by Wyatt, and Wyatt and Phillips, to a variety of particle types in the sense that the parameterized particle structure so-derived has been both physically reasonable and in agreement with values derived from other methods.

The validity of the aforementioned "inversion" technique has never been proven formally except for a very simple two-dimensional case. R. Mirales has shown that a least squares' fit of experimental differential light scattering data will yield a unique dielectric value and size for the case of an infinite homogeneous cylinder. Nevertheless, the technique, at least for spherically symmetric scatterers, has become quite standard, though still rigorously unproven. It should be pointed out, however, that there are certain types of dielectric structures that scattering measurements cannot "sense". These include certain non-scattering, or "invisible" particles in the Kerker sense as well as structures within regions through which the incident wave cannot penetrate. For example, any material inside of a perfect conducting region will not contribute to the scattered waves. Also, particles of very high refractive index (real or complex) will not permit much penetration of the incident wave and preclude, therefore, deduction of some internal dielectric features.

Despite the success of the simple least squares fitting technique and its utility for even complex particle structures, there are some obvious problems with the method. Consider a homogeneous, isotropic, spherical particle. Only two physical parameters completely describe this particle at a fixed wavelength of incident light: its radius R and refractive index n. Depending upon the particle size, however, even the simplest scattering measurement can yield a very detailed scattering pattern. For example, relief plots made by Pendorf of the scattering properties of a single particle of refractive index 1.33 for vertically polarized incident light showed enormous variations of scattered intensity with angle (differential light scattering) as a function of size. These plots showed, furthermore, that as the particle size increases, the angular scattering pattern becomes more complex. Because of this complexity, more detailed measurements of the light scattering properties of individual particles have been made, often yielding hundreds of data points for larger particles. Yet only two physical parameters R and n characterize the particle exactly. Why should it be necessary to make so many measurements to derive so few parameters?

The same question may also be raised concerning more complex homogeneous particle structures such as rods (3 physical parameters: length, radius, and refractive index), ellipsoids (4 physical parameters: 3 semi-axes and refractive index), simple flakes (4 parameters: thickness, length, width, refractive index) homogeneous absorbing spheres (3 parameters: radius and real and imaginary parts of refractive index), etc. The present invention describes a method and apparatus by which means particle characterization may be achieved with fewer measurements, and greater accuracy in shorter time periods than has heretofore been possible.

SUMMARY OF THE INVENTION

Figure 1:
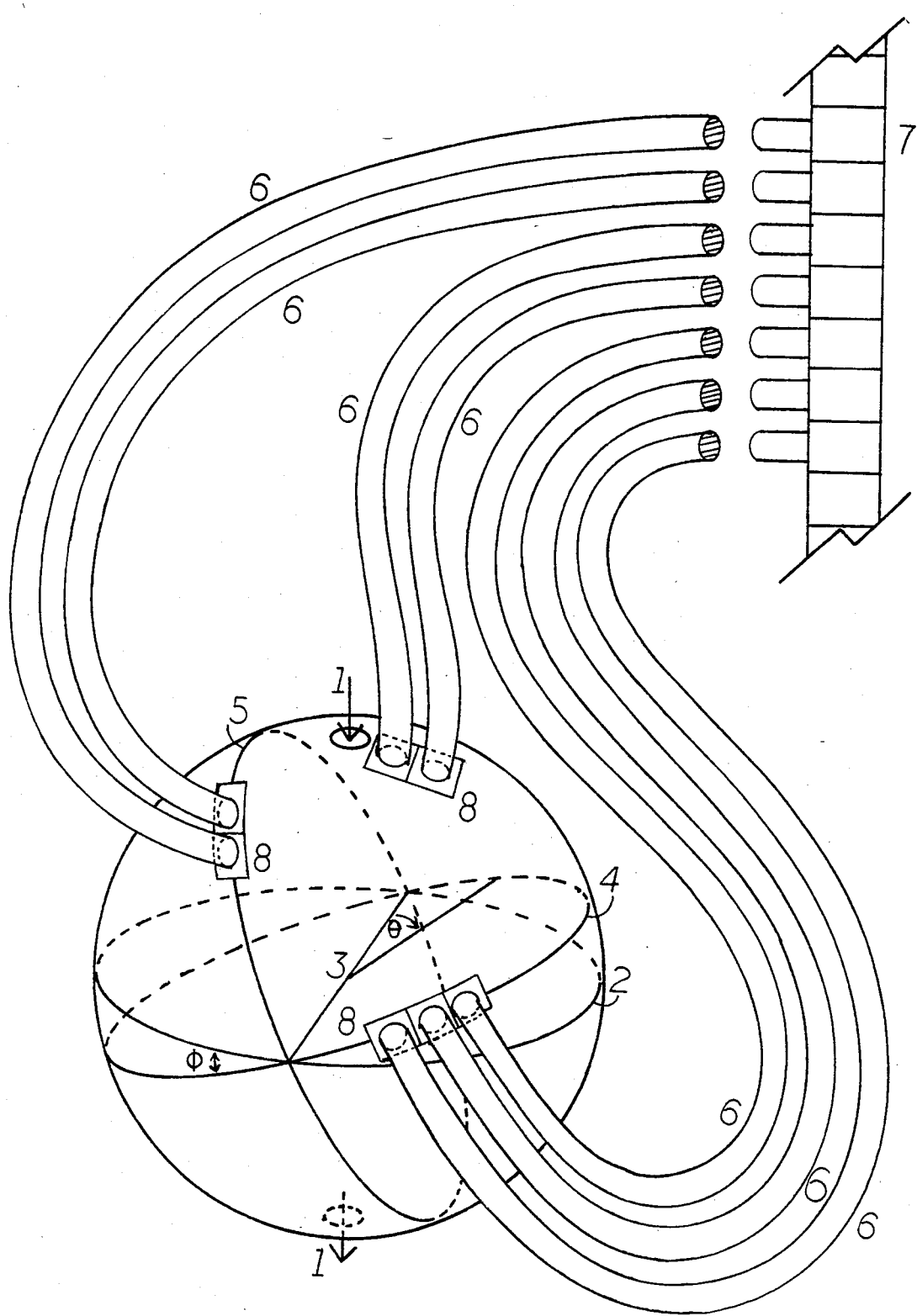
FIG. 1 is a schematic of the scattering geometry associated with a light scattering measurement over a spherical surface. The figure shows the planes of polarization, laser orientation, detector positions, and the aerosol stream entrance and exit apertures.

FIG. 1 shows in schematic form the preferred embodiment of the invention. A gas stream contains entrained microparticles which enter and exit one-at-a-time through the poles, respectively, of a spherical structure 1 equidistant from the point of intersection of the laser beam and the gas stream. Perpendicular to this stream and lying in the equatorial (E) plane 2 of the sphere is a light or laser beam 3 preferably plane polarized perpendicular to the V-plane 4 and parallel to the H-plane 5.

Over the surface of this sphere are numerous pairs of optical fibers 6 or other means to transmit the signals received thereby to detector means 7. The light scattering signals originating during the traversal of the laser beam by a particle are detected and subsequently stored.

Figure 2:
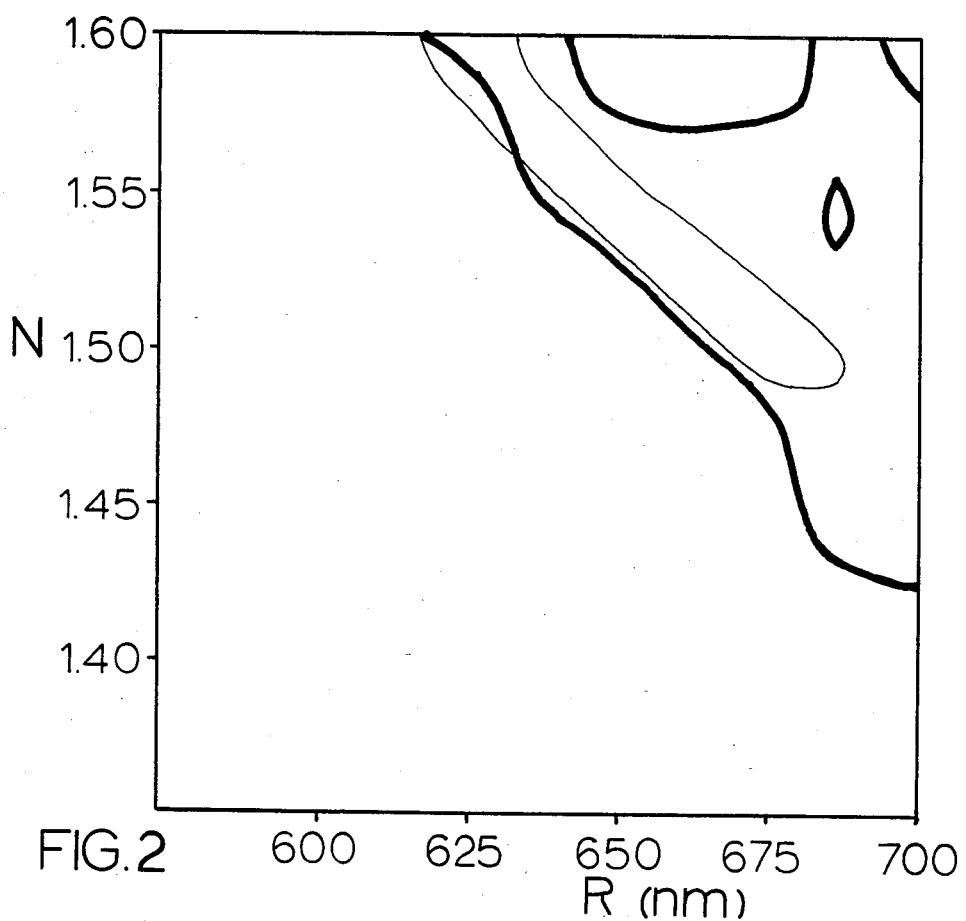
FIG. 2 shows the overlap of two strip maps within a specified range of refractive index and particle size.
Figure 3:
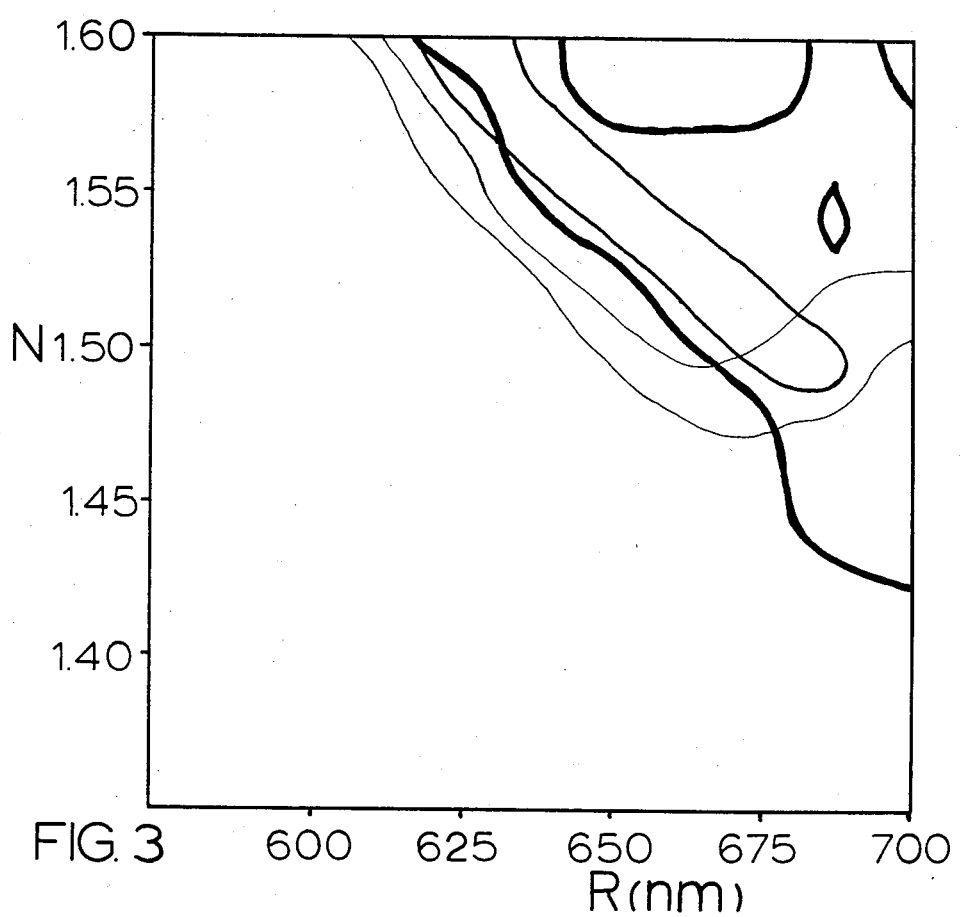
FIG. 3 shows the overlap of the previous two strip maps with a third strip map, again within the same refractive index and particle size ranges.

The identification of the particles, one at a time, is achieved by means of a computer overlay of sets of strip maps. A strip map is defined as a graphical, or computerized representation of a particular optical observable or measurement over a range of that observable. For example, for the case of a simple spherical particle whose radius R lies between 600 and 700 nanometers and with a refractive index n between 1.4 and 1.6, FIG. 2 shows the overlap of two strip maps in this range. The darker boundary, containing a small hole, surrounds all R/n pairs yielding six scattered intensity maxima as measured in the plane 4 of FIG. 1 for scattering angle $\theta$ between 5° and 175° with respect to the direction of the laser beam indicated. The lighter boundary surrounds all R/n pairs yielding a ratio $\rho_1 = I_v(20°)/I_H(90°)$ between 0 and 1, where $I_v(20°)$ is the intensity of light detected at $\theta = 20°$ in plane 4 of FIG. 1, and $I_H(90°)$ is the intensity of light detected at $\theta = (90°)$ in plane 5. If we consider two other optical observable ratios $\rho_2 = I_v(180°)/I_H(90°)$ and $\rho_3 = I_v(90°)/I_H(90°)$, where for the strips or regions indicated $4.5 < \rho_2 < 6.0$ and $1.0 < \rho_3 < 1.6$, then the four corresponding overlapped strip maps would yield FIG. 3. The dark shaded region, corresponding to the region of common overlap of all four strips, has a geometrical center corresponding approximately to R=685 nm and n=1.51. For a homogeneous sphere of radius 680 nm and n=1.50, illuminated with vertically polarized light at 632.8 nm, the number of scattering maxima produced in plane 4 of FIG. 1 is 6, $\rho_1 = 0.72$, $\rho_2 = 5.35$, and $\rho_3 = 1.17$. For the data from this particle, therefore, the strip maps resulting in FIG. 3 would have yielded the derived particle parameters R=685 nm and n=1.51 as described. This is an excellent representation of the actual particle parameters R=680 nm and n=1.50 and confirms the method.

PRINCIPLES OF THE INVENTION

A new method by which means the physical parameters of micriparticle structures may be derived rapidly and with great accuracy, called the "optical strip method" forms the basis for the major types of optical measurements that the apparatus will make. The method consists simply in the storage of certain theoretical (or experimentally determined) optical observables on maps which are then overlayed to yield the required physical parameters. As an example, we have good reason to believe that the deduction of the two physical parameters for any homogeneous, non-absorbing spherical particle can be determined within less than a millisecond from only four or five optical observables. The derived values will have an accuracy of about 1% despite the experimental values having a greater uncertainty. The success of the approach for spheres leads us to state that the physical properties of far more complex particles will be derivable from similar measurements.

Before discussing the optical strip method, the basic geometry of the proposed light scattering measurement is explained. FIG. 1 shows the light scattering chamber in schematic form. Particles enter at the top of the spherical structure entrained in a laminar flow stream. The equatorial plane normal to this flow direction is shown together with planes labeled V(4) and H(5) respectively. In the preferred embodiment, plane V makes an angle of about 22° with respect to the equatorial plane and plane H is at 90° to plane V. This important feature of the preferred embodiment permits scattered light intensities to be measured at all angles along planes 4 and 5 while providing non-interfering means 1 for the aerosol stream. Were it not for the tilting of plane 4, the entrance and exit ports 1 would interfere with measurements made in plane 5 in the forward and back scattering directions. Planes 4 and 5 intersect in a line lying on the equatorial plane 2 and it is along this line that the incident laser beam 3 lies. The laser is plane polarized with its electric field normal to the plane 4, i.e. it is vertically polarized with respect to 4. It is, therefore, horizontally polarized with respect to plane 5. The tilting of planes 4 and 5 with respect to the equatorial plane 2 has an important consequence: With suitable detectors lying in planes 4 and 5, the orifices required to bring the microparticles through the system will not obstruct any light scattering measurements in these important planes. Over the surface of the sphere are placed approximately 200 masks, 8. Attached to each one is a uniform optical fiber bundle 6 carrying its signal to the fiber optics faceplate 7 of a curved microchannel plate of a design such as manufactured by the Ball Corporation. The masks 8 are another important feature of the preferred embodiment. In the forward direction they are very small, perhaps only 1% of the area of those in the side and backscattered directions. This concept extends considerably the dynamic range of the system, permitting particles of great size disparity to be measured without sacrificing precision in recording the large variations of scattered intensity. The masks are covered with polarizing means to permit measurement of specific polarization states of the detected radiation.

Consider now the determination of a particle's shape by means of the preferred embodiment. At the time a particle strikes the laser beam at a point equidistant from all masks 8, a spherical pulse emanates from the particle and its vertical scattering pattern is detected in the V plane, 4. At the same time the horizontal scattering pattern would be detected in the H plane, 5. If the azimuthal angle $\phi$ is measured around the axis defined by the direction of the laser beam with the V plane 4 corresponding to $\phi=0$ then the intensity of scattered light per unit solid angle from a spherically symmetric particle at the angle $(\theta,\phi)$ as given, for example, by Wyatt in 1968 is:

$$I(\theta,\phi) = \frac{\lambda^2}{4\pi^2}[i_1(\theta)\sin^2\phi + i_2(\theta)\cos^2\phi], \quad (1)$$

where $$i_1(\theta) = \sum_{l=1}^{\infty} \frac{(2l+1)}{l(l+1)} [{}^eB_l\pi_l(\cos\theta) + {}^mB_l\tau_l(\cos\theta)]|^2 \quad (2)$$

and $$i_2(\theta) = \sum_{l=1}^{\infty} \frac{(2l+1)}{l(l+1)} [{}^eB_l\tau_l(\cos\theta) + {}^mB_l\pi_l(\cos\theta)]|^2 \quad (3)$$

The coefficients ${}^eB_l$ and ${}^mB_l$ are complex functions of the particle's spherically symmetric structure and the angular functions $\pi_l$ and $\tau_l$ may be expressed in terms of the Legendre polynomials $P_l(\cos\theta)$ and $P_l^1(\cos\theta)$ as $$\pi_l(\cos\theta) = P_l^1(\cos\theta)/\sin\theta \quad (5)$$

$$\tau_l(\cos\theta) = \frac{-\partial^2}{\partial\theta^2} P_l(\cos\theta),$$

If one measures $i_1(\theta)$ at a particular value of $\theta$ in the H-plane 5 ($\theta=\pi/2$) and $i_2(\theta)$ at the same value of $\theta$ in the V-plane 4 ($\theta=0$), then the intensity measurement at some arbitrary $\phi$ between 0 and $\pi/2$ must be given by EQ. (1). Since the three quantities $i_1$, $i_2$, and $I(\theta,\phi)$ are absolute, the confirmation of spherical symmetry is best achieved by installing two detectors at the point $(\theta,\phi)$ each covered by a polarized analyser to measure, respectively, the intensity of light polarized in the $\phi$ and $\theta$ directions (corresponding to V and H polarizations). The ratio of these latter intensities must therefore equal the measured ratio $i_2/i_1$ times $\tan^2\phi$. Any departure from this simple result must correspond to a departure of the scattering particle from spherical symmetry. For a few values of $\theta$, therefore, a measurement of $i_1(\theta)$, $i_2(\theta)$ and the polarization ratio at $\phi$ will confirm unambiguously a particle's asphericity. Suitably interpreted, measurement of these off-planar values can also yield particle shape.

Figure 4:
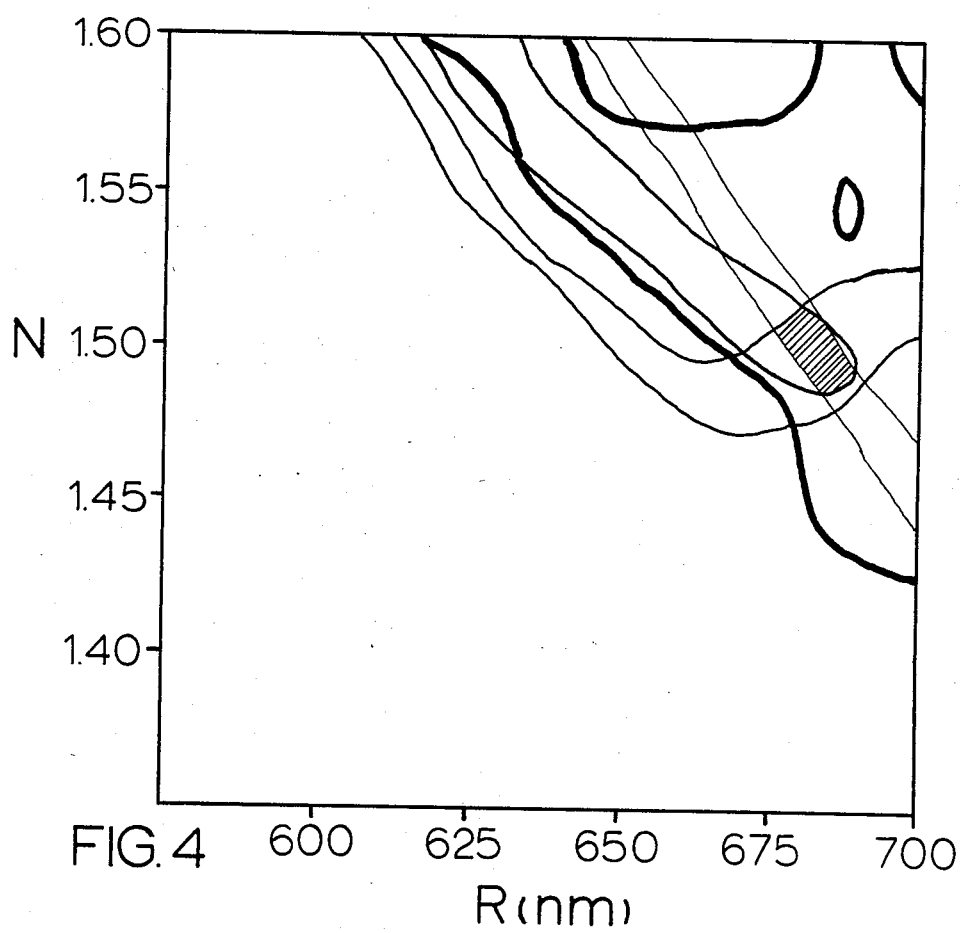
FIG. 4 shows the overlap of the previous three strip maps with a fourth strip map.
Figure 5:
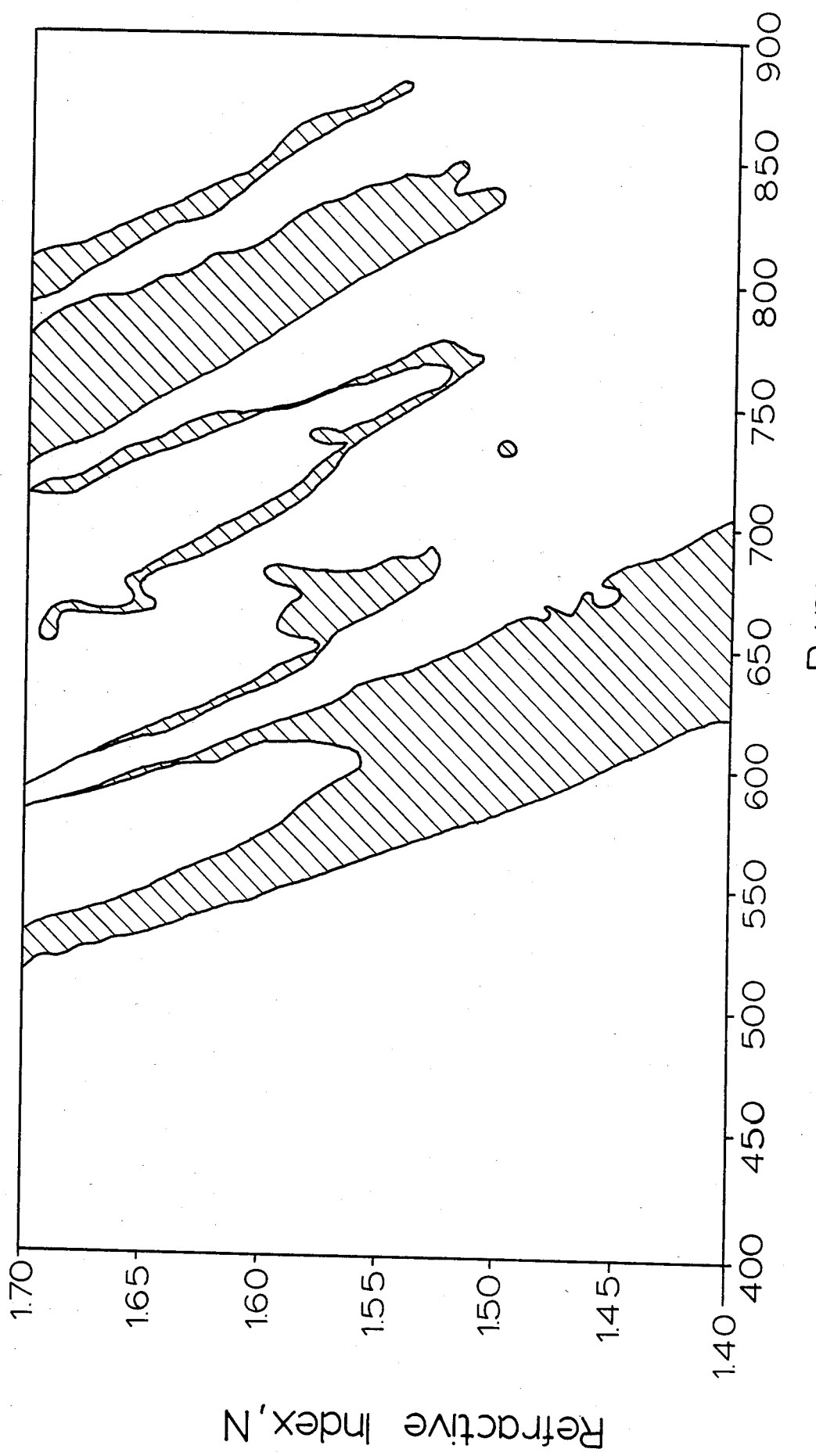
FIG. 5 shows a different strip map over a larger range of physical parameters.

Returning now to the optical strip method, consider, for example, plotting a line corresponding to all particle radius, R, and refractive index, n, values yielding a ratio $\rho_1$ of the intensity of light scattered at $\theta=20°$ in the V-plane 4 to the intensity of light scattered at $\theta=90°$ in the H-plane of less than $10^{-4}$, for example. The incident light in the preferred embodiment is monochromatic and vertically polarized with respect to the V-plane 4. Such a line represents a contour of near-$0\rho_1$ values. Next plot a region or strip of $\rho_1$ lying between two contours, say 0 and 1.0. FIG. 2 shows such a resulting strip map for the optical observable ratio $\rho_1$, where $\rho_1 = I_V(20°)/I_H(90°)$, $I_V(20°)$ is the intensity of light measured in the V-plane 4 at $\theta=20°$; $I_H(90°)$ is the intensity of light measured in the H-plane 5 at $\theta=90°$, and $0<\rho_1<1$. The observable $\rho_1$ is surrounded by the light closed curve shown in FIG. 2 within the restricted R/n ranges presented in FIG. 2 by 600 nm$\leq$R$\leq$700 nm and 1.4$\leq$n$\leq$1.6. Next consider a similar strip map of all R, n points yielding a total of 6 scattering peaks in the V-plane 4 in addition to the forward scattering and back scattering peak (if any). FIG. 2 shows this strip map represented by the dark boundaries (note small hole) overlapping the earlier $\rho_1$ strip over a similar range of n and R. Adding another observable $\rho_2 = I_V(180°)/I_H(90°)$ for 4.5$\leq\rho_2\leq$6.0 would result in the strip map of FIG. 3 and finally the third strip map showing the ratio $\rho_3 = I_V(90°)/I_H(90°)$, for 1.0$\leq\rho_3\leq$1.6 is indicated in FIG. 4. Selecting the geometric center of the unique quadruple overlap region to calculate the "best" values of n and R, yields n=1.5±0.01 and R-685±5 nm. Most important, of course, is the fact that three relatively simple optical observables, when combined with the number of peaks in the V plane yields an immediate result. Many other light scattering observables have been examined and their corresponding strip maps are now routinely generated by a computer program. An example is presented in FIG. 5 over a broader range of both n and R, the outlined region corresponding to five scattering peaks.

The implementation of the strip map technique in the preferred embodiment is relatively straightforward. The maps are stored in the memory of a computer, such as the microprocessor system Universe 68115 as manufactured by the Charles River Data Systems, in a very compact form since the presence or absence of the observable in the range specified may be represented by the binary bit 1 or 0, respectively. In order to cover a range of refractive index between 1.20 and 4.0 and a range of radii between 200 and 1500 nm, for example, less than 64,000 bytes of memory are required to store all the associated maps for each of four optical observables. For the case of spheres, readily detected as described above, whose optical observable strip maps are stored and based on four optical observables, approximately 700 $\mu$sec would be required for identification using an array processor, such as the CHI 5 as manufactured by CHI Systems, Inc. Since the transit time of a microparticle through a 1 mm laser beam itself would, in the preferred embodiment, occupy about 1 to 2 ms, this processing time, which can be performed in parallel with a subsequent measurement, could even be expanded considerably without sacrificing throughput rate. Thus it is seen that the preferred embodiment containing an array processor results in an apparatus capable of identifying microparticles in real time at a rate in excess 10,000 per minute.

Other sets of strip map algorithms and observables for the other types of particle structures of interest may be generated and stored. For even relatively complex structures, these maps may be calculated following the methods developed by Barber and others. Alternatively, strip map observables may be measured experimentally and stored subsequently. The deduction of particulate refractive index is the most important key to particulate identification. The refractive indices of such diverse particles as bacteria, spores, latex, flyash, and photochemical smog, to name but a few, appear to fall within unique ranges and provide thereby, an excellent means for particle identification.

The preferred embodiment of the proposed system includes means for the performance of additional types of optical measurements which, for certain classes of particles, could yield types of optical observables other than those generated from elastic light scattering methods. After a given microparticle has traversed the chamber in which its light scattering properties have been measured, it could pass subsequently through other beams of electromagnetic radiation that might, for example, stimulate fluorescence, or a white light beam whose scattering could yield important variations of refractive index with wavelength. Depending upon the types of particles whose identification is required, specific types of additional optical observables so obtained are combined by the computer of the preferred embodiment to yield additionally deduced structural parameters.

As discussed above, these are two key elements of the particle characterization system: hardware for the detailed measurement of the light scattering signature of each particle and a computer/software interface that permits the real time characterization of the particle from this signature. Also stressed is provision for the subsequent measurement of other optical observables, such as fluorescence and white light scattering.

Figure 6:
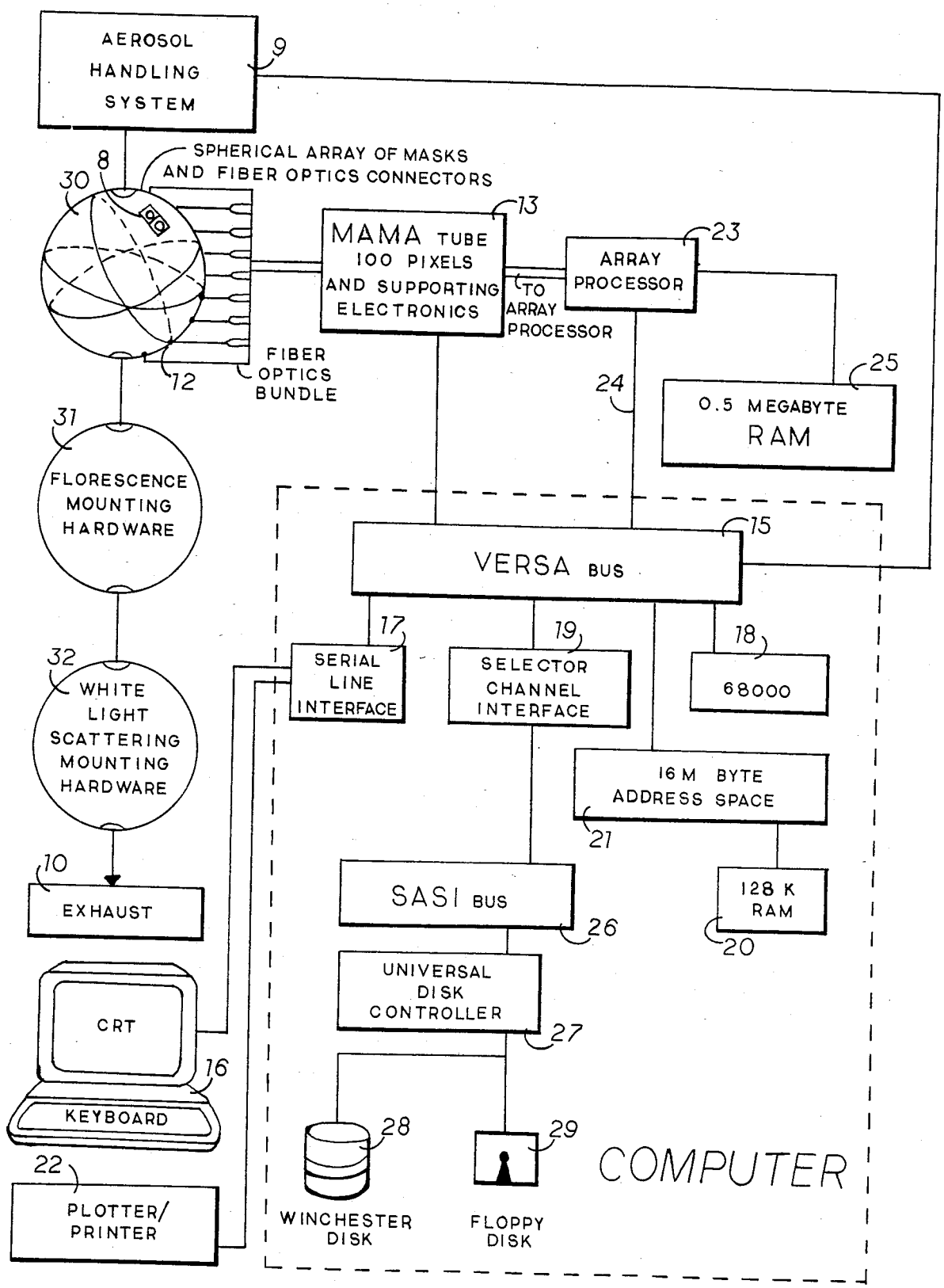
FIG. 6 shows a schematic diagram of the principal elements of an aerosol analyser based on measurement of various optical observables.

Certain important components of the preferred system are commercially available. This is particularly true for some of its most complex elements, the detection and computer hardware. FIG. 6 presents a schematic overview of the preferred embodiments of a particle identification system. The aerosol handling system 9 is of the type incorporated in the Royco or Climet air sampling instruments. These laminar flow aerosol sampling systems consist generally of a design developed by NASA. A clean air sheath surrounds the aerosol stream which is pulled through the system by means of a vacuum at the exhaust port 10. The aerosol flow speed is regulated by the vacuum head and the particle density is controlled by varying the clean air intake orifice size. Both particle speed and density are controlled by means of a feedback circuit in the computer 11 and sensed by dedicating a single detector 12 to this task.

The basic light scattering detection system of the preferred embodiment consist of two 100 anode pixel multi-anode microchannel array 13 (MAMA) tubes of the type manufactured by Litton Industries Tube Division complete with electronics and fiber optics of the type developed by Ball Corporation. Each anode, or pixel structure and the 20–40 microchannels that supply it with photoelectrons is the equivalent of a conventional photomultiplier tube. Thus a 100 pixel MAMA tube is the equivalent of 100 photomultipliers. Each particle should be illuminated for a period of about 1 to 2 ms for a nominal beam diameter of 1 mm or less.

The MAMA detector system essentially counts photons with an overall quantum efficiency of about 10% in the red region of the spectrum. Each pixel yields a linear response to its incident bursts of photoelectrons up to about 1 MHz. In a 1 ms period each mask 8 of the preferred embodiment should permit, therefore, no more than $10^3$ photons to be counted. Thus no fiber optic mask has an incident flux in excess of $10^4$ photons per ms. A linearly polarized He—Ne laser of the type manufactured by Spectra Physics, for example, operating at a wavelength of 632.8 nm and with a power of about $10^{-2}$ watt is sufficient for the preferred system. At this power, a particle of diameter 200 nm will scatter about $10^6$ photons within a period of a ms. Masked optical fiber elements are attached over the surface of an easily removed and cleaned spherical scattering chamber. In the preferred embodiment, these masks are of various diameters consistent with the aforementioned photon flux requirement. In the forward scattering directions, these masks subtend preferably an effective solid angle 0.05 steradian, while in the backward directions they may subtend almost ten times that amount.

As the photons are detected by the MAMA array, their counts are stored in a set of 100 RAM words which are then transferred into a computer system, such as a Charles River Data System UV68/15 computer 11 shown as a component in FIG. 6, or for real time analysis using strip map techniques, into an array processor 23 of CHI 5 type as manufactured by CHI Systems, Inc. After each set is transferred, the MAMA RAM's are cleared to await the photon counts of the next particle. Such a computer system in the preferred embodiment of this invention should include means via an interface Versa bus 15 of the type developed by the Motorola Company to permit control by the user from a CRT keyboard 16 of the type VT100 manufactured by Vector Graphic Inc. through a serial line interface means 17. This same bus 15 permits access to the on-line computer 18 of the type 68000 manufactured by Motorola, a selector channel interface 19, and a large 128K RAM 20 providing 16M byte address space 21. An off line printer and plotter 22 is also connected through the serial interface 17 to provide means for the reporting of stored or processed data. The MAMA tube electronics assembly 13 provides means for storage of each pixel output count in the computer RAM 20 or a special RAM 22 connected through the array processor 23. The array processor RAM 22 is preferably of large size to permit the on-line identification of microparticles by means of the array processor 23 itself. As the array processor 23 completes its analyses by means of strip maps stored in its high speed RAM 22, the results are transmitted through means 24 to the Versa bus 15 and thence into a selector channel interface 25 connected to another bus 26 of the type developed by Shugart. Through this bus 26 a universal disk controller 27 selects storage means 28 or 29 on which the processed data from the array processor 23 are stored. Alternatively, the data processed by the array processor 23 may be transferred through means 15 and 21 to memory 20 for further parallel processing by the computer means 18.

As discussed earlier, the preferred embodiment of the invention should include auxiliary means for the subsequent measurement of further optical observables of each microparticle as it leaves the light scattering chamber 30 of FIG. 8. This would include, but not be limited to, means 31 for fluorescence measurements on the flowing single particles by illuminating them with an ultraviolet source such as a laser of the type manufactured by Liconix producing continuous radiation at 330 nm. Detection means not shown could be similar to those of the scattering chamber 30 or include spectrographic means to transmit fluorescence spectral variations directly to the array processor 23 via a set of MAMA pixels similar to means 13, but storing spectral intensity variations. Subsequent means such as 32 for the performance of white light scattering experiments may also be inserted into the particle beam of the preferred embodiment.

Although the aforementioned discussion has been directed primarily to the identification and characterization of single microparticles, this invention is also applicable to measurements of many particles simultaneously, such as would be found in a suspension. In addition, just as the measurement of a set of optical observables from an unknown particle or ensemble of particles may be used as herein described to identify or characterize it, inversely a known particle or ensemble of particles may be uniquely characterized by associating with it its measured optical observables. Thus a spherical particle of radius 680 nm and refractive index 1.5 would equally well be characterized as a spherical particle producing 6 peaks in the V-plane and having observables $\rho_1$, $\rho_2$ and $\rho_3$ given by 0.72, 5.35, and 1.17, respectively, at a wavelength of 632.8 nm. Similar sets of optical observables may be used to characterize ensembles of scattering particles such as found in beverages or colloidal suspensions and compare such fluids with unknown fluids as might be required for quality control of these fluids.

While there has hereinbefore been presented what are at present considered to be the preferred embodiment or methods, it will be apparent to those of ordinary skill in the art that many modifications and variations of the art taught herein may be made therefrom without departing from the true spirit and scope of the invention. All such variations and modifications, therefore, are considered to be a part of the invention.

What is claimed is:

1. A process for characterizing and identifying a single unknown microparticle within a range of interest on the basis of physical properties derived from measured optical observables comprising the steps of:
   A. Introducing microparticles one-at-a-time into a flowing laminar stream surrounded by a particle-free sheath of the same material as the stream;
   B. Passing said stream containing said entrained microparticles through a narrow beam of electromagnetic radiation;
   C. Surrounding said radiation beam and microparticle stream by means able to support a number of discrete detector means at selected angular locations about said radiation beam and microparticle stream, with said support means not obstructing the entrance and exit of either particle stream or radiation beam from said surrounding region and said number and locations of detector means being sufficient to yield a unique range of optical observable values characteristic of that expected from the microparticles of interest;
   D. Detecting the radiation scattered by each said microparticle as it passes through the radiation beam at each of the selected surrounding detector means;
   E. Converting each said detected scattered radiation intensity into a proportional numerical value;
   F. Storing said numerical values in a memory means with separate memory means corresponding to each discrete detector means;
   G. Deriving measured optical observable values by combining sufficient selected sets of stored numerical values to yield a set of optical observables spanning the range of observables characteristic of the particles of interest;
   H. Defining an optical observable map for a fixed range of optical observable values in terms of a set of physical parameters, each physical parameter restricted to a domain encompassing those characteristic of the microparticles of interest, and said map consisting of closed regions within which ranges the circumscribing physical parameters would result in an optical observable within the defining fixed range;
   I. Retrieving from memory means previously stored maps of optical observables, one map for each measured optical observable value and whose range of optical observable values bracket the corresponding computed value;
   J. Superimposing a sufficient number of said retrieved maps of optical observables to yield a unique and finite region of overlap;
   K. Identifying the range of each particle's physical parameters corresponding to the common overlap region of said retrieved maps; and
   L. Classifying and identifying the unknown microparticle by the values of the physical parameters defined by the optical observable map overlap region.

2. The process of claim 1 where the stream is a gas.

3. The process of claim 1 where the electromagnetic radiation is polarized.

4. The process of claim 3 where the optical observables include sets of ratios for measurements in the plane perpendicular to the electric field of the incident radiation normalized to a single value in the plane parallel to the incident electric field.

5. The process of claim 3 where an optical observable is the number of peaks in the plane perpendicular to the electric field of the incident radiation.

6. The process of claim 1 where the electromagnetic radiation is monochromatic and produced by a laser.

7. The process of claim 1 where the radiation is white light.

8. The process of claim 1 where the radiation is at a wavelength that causes the microparticles to fluoresce.

9. An apparatus for the characterization and identification of a microparticle by measurement of its optical observables containing
   A. Means for introducing microparticles one at a time into a flowing laminar stream surrounded by a particle-free sheath of the same material of the stream;
   B. Means for directing said stream containing said entrained microparticles through a narrow beam of electromagnetic radiation;
   C. Means, surrounding said radiation beam and microparticle stream, able to support a number of discrete detector means at selected angular locations about said radiation beam and microparticle stream, with said support means not obstructing the entrance and exit of either particle stream or radiation beam from said surrounding region and said number and locations of detector means being sufficient to yield a unique range of optical observable values characteristic of that expected from the microparticles of interest;
   D. Means for detecting the radiation scattered by each said microparticle as it passes through the radiation beam at each of the selected surrounding detector means;
   E. Means for converting each said detected scattered radiation intensity into a proportional numerical value;
   F. Means for storing said numerical values in a memory means with separate memory means corresponding to each discrete detector means;
   G. Means for deriving measured optical observable values by combining sufficient selected sets of stored numerical values to yield a set of optical obervables spanning the range of observables characteristic of the particles of interest;

F. Means for passing said microparticle into subsequent electromagnetic beams, each beam and region of microparticle intersection being surrounded by detection means as in D, above;

G. Means for repeating steps E to G above for each said subsequent electromagnetic field region;

H. Means for collecting all said optical obervables of steps G through I and processing in a computer means to yield a combined set of optical observables, one subset of said combined set corresponding to the measurements with respect to each interaction of said microparticle with each electromagnetic beam.

10. The apparatus of claim 9 where the stream is a gas.

11. The apparatus of claim 9 where the electromagnetic radiation is polarized.

12. The apparatus of claim 9 where the electromagnetic radiation is monochromatic and produced by a laser.

13. The apparatus of claim 9 where the interaction of said microparticle and one of said electromagnetic beams causes said particle to emit fluorescent radiation.

14. The apparatus of claim 9 where one of said electromagnetic beams is white light.

15. The apparatus of claim 9 where each detector means receives scattered radiation from said microparticle by optical fiber means.

16. The apparatus of claim 9 where selected detector means have attached thereto aperture means to restrict the amount of radiation incident thereon.

* * * * *